(12) United States Patent
Knauf et al.

(10) Patent No.: US 9,796,669 B2
(45) Date of Patent: Oct. 24, 2017

(54) PROCESS FOR PREPARING ISOCYANATES

(71) Applicant: Covestro Deutschland AG, Leverkusen (DE)

(72) Inventors: Thomas Knauf, Dormagen (DE); Andreas Karl Rausch, Kaarst (DE); Charles Bjoerndahl, Aukrug-Boken (DE); Matthias Ehlers, Marne (DE); Peter Plathen, Krefeld (DE); Carlos Alvarez Herrero, Tarragona (ES); Francisco Munoz Velasco, Tarragona (ES)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/128,813

(22) PCT Filed: Mar. 24, 2015

(86) PCT No.: PCT/EP2015/056183
§ 371 (c)(1),
(2) Date: Sep. 23, 2016

(87) PCT Pub. No.: WO2015/144658
PCT Pub. Date: Oct. 1, 2015

(65) Prior Publication Data
US 2017/0101368 A1     Apr. 13, 2017

(30) Foreign Application Priority Data

Mar. 27, 2014 (EP) .................................. 14162003

(51) Int. Cl.
*C07C 263/00* (2006.01)
*C07C 263/10* (2006.01)

(52) U.S. Cl.
CPC .................................. *C07C 263/10* (2013.01)

(58) Field of Classification Search
CPC .......................... C07C 263/10; C07C 265/14
See application file for complete search history.

(56) References Cited

U.S. PATENT DOCUMENTS

| | | | |
|---|---|---|---|
| 2,822,373 A | 2/1958 | Beck | |
| 2,908,703 A | 10/1959 | Latourette et al. | |
| 4,851,570 A | 7/1989 | Zaby et al. | |
| 5,136,087 A | 8/1992 | Van Horn et al. | |
| 5,599,968 A | 2/1997 | Bankwitz et al. | |
| 6,683,204 B1 | 1/2004 | Stamm et al. | |
| 7,038,002 B2 | 5/2006 | Pirkl et al. | |
| 7,118,653 B2 | 10/2006 | Brady et al. | |
| 7,547,801 B2* | 6/2009 | Pohl | C07C 263/10 560/347 |
| 7,592,479 B2 | 9/2009 | Stroefer et al. | |
| 7,851,648 B2 | 12/2010 | Sohn et al. | |
| 8,079,752 B2 | 12/2011 | Rausch et al. | |
| 8,097,751 B2 | 1/2012 | Koch et al. | |
| 8,546,606 B2 | 10/2013 | Brodhagen et al. | |
| 2010/0298596 A1 | 11/2010 | Keggenhoff et al. | |
| 2011/0301380 A1* | 12/2011 | Knoesche | C07C 263/10 560/347 |
| 2012/0095255 A1* | 4/2012 | Mattke | C07C 263/10 560/347 |
| 2013/0060062 A1* | 3/2013 | Mattke | C07C 263/10 560/347 |

FOREIGN PATENT DOCUMENTS

| | | | |
|---|---|---|---|
| DE | 3744001 C1 | | 6/1989 |
| WO | WO2013029918 | * | 2/2013 |
| WO | 2013029918 A1 | | 3/2013 |

OTHER PUBLICATIONS

WO2013029918 translated 2013.*
Wegener, Gerhard et al; "Trends in industrial catalysis in the polyurethane industry"; Applied Catalysis A: General 221; (2001); pp. 303-335; Elsevier Science B.V.; Dormagen, Germany.
Siefken, Werner; "Mono- und Polyisocyanate IV. Mitteilung Uber Polyurethane*)"; Justus Liebigs ; Dec. 11, 1948; pp. 75-106; Annalen Der Chemie. 562. Band; Leverkusen, Germany.
Eisenmann, Karl-Heinz et al; Ullmann's Encyclopedia of Industrial Chemistry; Isocyanate; Band 13; Hormone bis Keramik; 4th edition; (1977); pp. 351-353; Verlag Chemie-Weinheim-New York.

* cited by examiner

*Primary Examiner* — Yevegeny Valenrod
*Assistant Examiner* — Blaine G Doletski
(74) *Attorney, Agent, or Firm* — Donald R. Palladino

(57) ABSTRACT

The invention relates to a method for preparing isocyanates by the phosgenation of the corresponding amines in which problems resulting from the formation of deposits in apparatuses of the reaction segment during activation (starting) and deactivation (termination) of the method can be prevented by processing measures, in particular ensuring that there is a surplus of phosgene relative to the phosgenating amine during the critical starting and termination steps of the method.

24 Claims, 1 Drawing Sheet

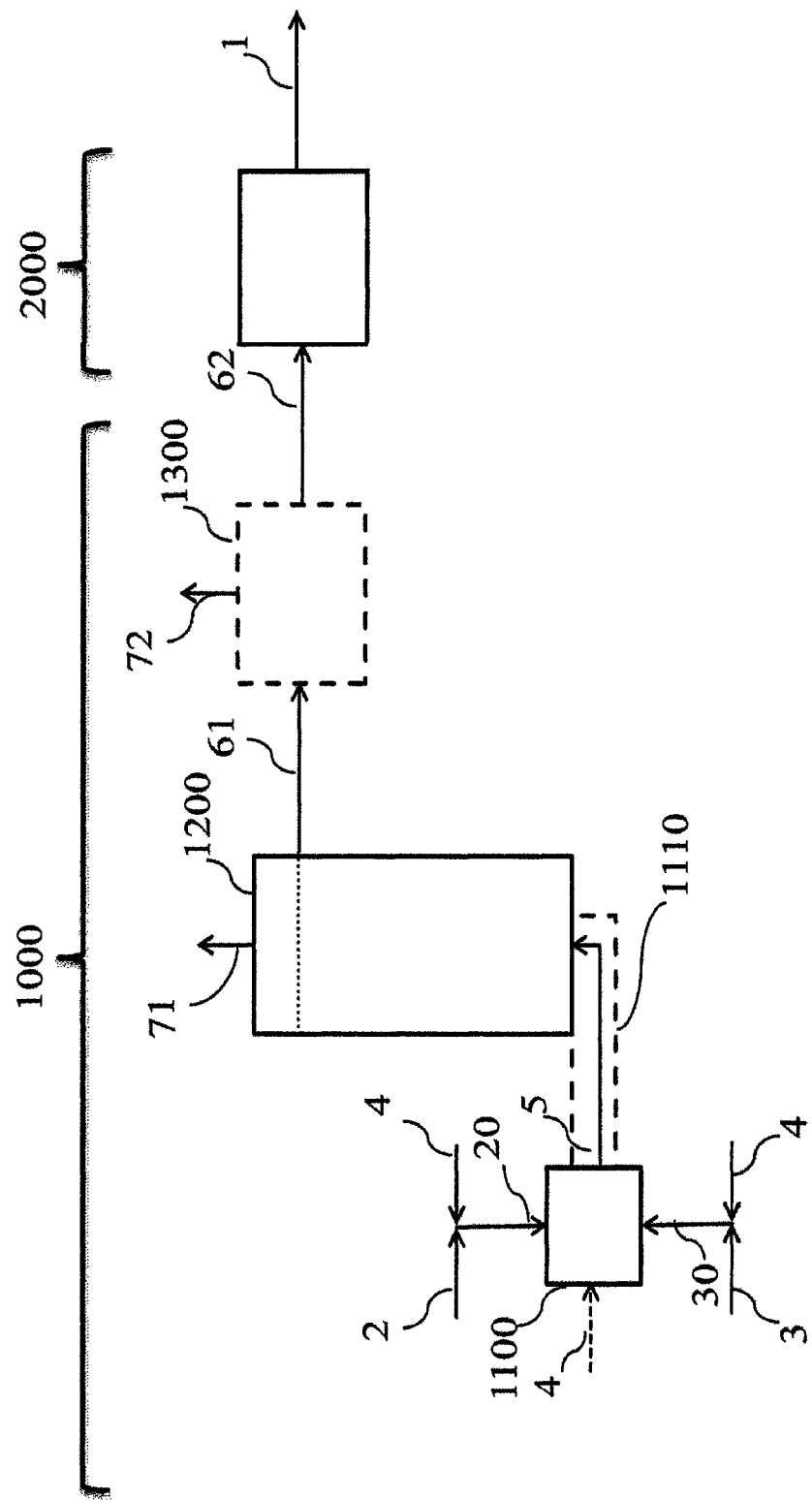

PROCESS FOR PREPARING ISOCYANATES

CROSS-REFERENCE TO RELATED APPLICATIONS

This Application is a National Phase Application of PCT/EP2015/056183, filed Mar. 24, 2015, which claims priority to European Application No. 14162003.9, filed Mar. 27, 2014, each of which being incorporated herein by reference.

FIELD

The invention relates to a process for preparing isocyanates by phosgenating the corresponding amines, in which problems resulting from the formation of deposits in apparatuses in the reaction section during the startup and shutdown of the process are avoided by chemical engineering measures, especially the assurance of an excess of phosgene over the amine to be phosgenated during the critical startup and shutdown steps of the process.

BACKGROUND

The industrial scale preparation of polyisocyanates by reacting the corresponding amines with phosgene has long been known from the prior art, the reaction being conducted in the gas or liquid phase and batchwise or continuously (W. Siefken, Liebigs Ann. 562, 75-106 (1949)). There have already been multiple descriptions of processes for preparing organic isocyanates from primary amines and phosgene; see, for example, Ullmanns Encyklopadie der technischen Chemie [Ullmann's Encyclopedia of Industrial Chemistry], 4th ed. (1977), volume 13, p. 351 to 353, and G. Wegener et al. Applied Catalysis A: General 221 (2001), p. 303-335, Elsevier Science B. V. There is global use both of aromatic isocyanates, for example methylene diphenyl diisocyanate (MMDI—"monomeric MDI"), polymethylene polyphenylene polyisocyanate (a mixture of MMDI and higher homologs, PMDI, "polymeric MDI") or tolylene diisocyanate (TDI), and of aliphatic isocyanates, for example hexamethylene diisocyanate (HDI) or isophorone diisocyanate (IPDI).

Modern industrial scale preparation of polyisocyanates is continuous, and the reaction is conducted as an adiabatic phosgenation as described in EP 1 616 857 B2. Unwanted deposits and by-products in the reactor are avoided through correct choice of reaction temperature and pressure. In the mixing space, a molar excess of phosgene relative to the primary amino groups should be ensured. A three-stage phosgenation line is described in EP 1 873 142 B1, in which the pressure between the first stage of a dynamic mixer and the second stage of a first phosgenation reactor remains the same or rises and, in the third stage, in an apparatus for phosgene removal, the pressure is lower than in the second stage.

WO 2013/029918 describes a process for preparing isocyanates by reacting the corresponding amines with phosgene, which can also be conducted at different loads on the plant without any problems, and more particularly, even when running the plant in the partial load range, the mixing and/or the reaction is said to proceed within the optimized residence time window in each case, by increasing the ratio of phosgene to amine or adding one or more inert substances to the phosgene and/or amine stream. The process of the invention is to enable operation of an existing plant at different loads with constant product and process quality. This is to dispense with the provision of several plants with different nameplate capacities.

The application teaches that essential parameters of a phosgenation, such as the residence times of the co-reactants in the individual apparatuses in particular, are optimized for the operation of the production plant at nameplate capacity, which can lead to problems in terms of yield and product purity when the plant is operated at lower than nameplate capacity (cf. page 2 lines 20 to 36). In order to be able to attain the optimized narrow residence time windows even at partial load (i.e. reduced amine flow rate compared to operation at nameplate capacity), it is suggested that either the phosgene stream and/or the inert fraction be increased (cf. page 3 lines 5 to 19), preferably in such a way that the total flow rate of all components corresponds essentially to that at nameplate capacity (cf. page 6 lines 4 to 8). The application does mention startup and shutdown operations in the description of the background of the invention claimed on page 2, but does not disclose either any technical teaching as to the specific actions by which a non-operational production plant (i.e. amine flow rate and phosgene flow rate equal to zero) is most advantageously brought to the desired operating state of the nameplate capacity nor any technical teaching as to the specific actions by which an operational production plant is most advantageously shut down (i.e. amine flow rate and phosgene flow rate equal to zero). The technical measures disclosed in the application (i.e. the increase in the phosgene flow rate and/or the inert fraction) should be considered exclusively in the context of the problem of operation (i.e. the amine flow rate is significantly greater than zero) of a production plant at lower than nameplate capacity, and of the problem of how a plant operated at nameplate capacity can advantageously be switched to operation at lower than nameplate capacity (see the examples). The document does not address the sequence of startup of individual streams in the startup operation or the shutdown of individual streams in the shutdown operation.

The reaction output from the phosgenation line can be worked up as described in EP 1 546 091 B1. The workup of the reaction product is effected in a layer evaporator, preferably a falling-film evaporator, in which phosgene and HCl are evaporated gently.

U.S. Pat. No. 5,136,087 (B) likewise describes the removal of phosgene from the reaction mixture of the phosgenation by means of an inert solvent vapor which may originate from the solvent recovery in the phosgenation plant.

One possible embodiment of the solvent removal and recovery is described in EP 1 854 783 A2. Di- and polyisocyanates of the diphenylmethane series (MDI) which have been obtained by reacting corresponding amines dissolved in a solvent with phosgene are first freed of hydrogen chloride and excess phosgene, and then a distillative separation of this crude solution into isocyanates and solvent is conducted. The solvent is recycled into the process to prepare solutions of the feedstocks of the polyisocyanate preparation. In the case of preparation of MDI using monochlorobenzene as solvent, this distillative separation can advantageously be effected in such a way that the crude isocyanate solution is worked up in two steps to give a bottom product containing at least 95% by weight of isocyanate, based on the weight of the isocyanate-containing stream, and this bottom product is subsequently preferably freed of low boilers in further steps. In the first step, 60%-90% of the solvent present in the crude isocyanate solution is removed, preferably by a flash distillation at absolute pressures of 600-1200 mbar and bottom temperatures of 110° C.-170° C., the vapors being worked up in a distillation column having 5-20 plates and 10%-30% reflux, so as to achieve a solvent-containing stream having a diisocyanate content of <100 ppm, preferably <50 ppm, more preferably <20 ppm, based on the weight of the solvent-containing stream. In the second step, the remaining solvent is removed down to a residual content of 1%-3% by weight in the bottom product at pressures of 60-140 mbar absolute and bottom temperatures of 130° C.-190° C. The vapors can likewise be worked up in a distillation column having 5-20 plates and 10%-40% reflux, so as to achieve a solvent-containing stream having a diisocyanate content of <100 ppm, preferably <50 ppm, more preferably <20 ppm, based on the weight of the solvent-containing stream, or this stream, after condensation, is recycled back into the first distillation step as feed. In the same way, the distillate streams removed in the subsequent steps can be recycled back into the first distillation step as feed.

Given suitable design of the distillation, the recycled solvent has the aforementioned diisocyanate contents. In addition, through use of suitable technical measures, it is possible to further increase the solvent quality with regard to diisocyanate content by, for example, wholly or partly removing diisocyanate-containing solvent mist or droplets in the vapors of the one-stage or multistage distillative solvent removal by means of a demister, baffle plate or hydrocyclone, or by quenching (spraying) with fresh or recycled solvent. Combinations of the aforementioned measures are also possible.

EP 1 854 783 A2 describes the quality demands that exist for a solvent for a process for preparing polyisocyanates. It has been found that the purity of the circulated solvent which is used for preparation of the amine solution used in the phosgenation is of crucial significance for the by-product formation in the crude isocyanate. Even a content of only 100 ppm phosgene or 100 ppm of diisocyanate, based on the weight of the solvent, leads to detectable by-product formation in the crude isocyanate. While this leads to a reduction in yield in the case of distilled isocyanates, i.e. in the case of the isocyanates obtained as top product, this causes an unwanted effect on the quality (color) and reaction characteristics in the case of the isocyanates obtained as bottom product, for example the di- and polyisocyanates of the diphenylmethane series. This is detectable, for example, via chlorinated secondary components and an elevated iron content.

Carbon tetrachloride as solvent impurity gets into the phosgenation circuit via the phosgene and accumulates in the solvent through the solvent circuit. With time, the concentration of carbon tetrachloride settles at a uniform level shaped by the losses of carbon tetrachloride via the discharge with the offgas. According to the process conditions, a solvent used in the phosgenation which has not been supplied fresh but comes from recycling streams within the process has a content by mass of carbon tetrachloride of 0.01% to 5%, and in some circumstances even up to 20%, based on the total mass of the solvent including all impurities.

DE-A-19942299 describes a process for preparing mono- and oligoisocyanates by phosgenating the corresponding amines, wherein a catalytic amount of a monoisocyanate is initially charged in an inert solvent together with phosgene, the amine is added, normally dissolved in the solvent, and the reaction mixture obtained is reacted with phosgene. The intermediate formation of sparingly soluble suspensions is avoided. The desired isocyanate, in the case of full conversion of the amine, is formed in high yields and high selectivity within distinctly shortened reaction times, without formation of symmetrically substituted N,N'-urea from the amine as by-product. However, the process is comparatively complicated and energy-intensive, particularly through use of the additional monoisocyanate which has to be removed again at a later stage.

Apart from a few exceptions, the prior art described is concerned only with processes in normal operation. Startup operations until attainment of a steady operating state at the desired target flow rate of the amine (called the "startup time") or shutdown operations until attainment of complete shutdown (called the "shutdown time") are not considered in the documents relating to continuous industrial scale processes. Only in documents in which batchwise phosgenation is described are startup phases given more detailed consideration; see, for example, U.S. Pat. No. 2,908,703 and U.S. Pat. No. 2,822,373. Unexpected downtime (for example an abruptly forced shutdown of the plant) also lead at short notice to process regimes which can differ significantly from those in normal operation.

SUMMARY

The present invention is concerned specifically with such deviations from normal operation in continuous processes for preparing di- and polyisocyanates by phosgenating the corresponding primary amines in the liquid phase. Startup and shutdown periods are a frequent everyday occurrence in industry and are not necessarily associated with opening or another mechanical intervention into the phosgenation plant, but merely with the shutdown and restarting of the phosgenation plant. It is generally a feature of these startup and shutdown periods that there can be deviations in the ratio of phosgene to amine. This is observed especially when the amount of amine to be converted per unit time (the amine flow rate) is very small compared to the operation of the plant at nameplate capacity. These variations in the ratio of phosgene to amine are disadvantageous, solids such as polyurea or amine hydrochloride can form and precipitate out to an increased extent. The same applies to unplanned, abrupt shutdowns of a phosgenation plant in normal operation.

Deviations from normal operation, whether they be planned or the result of unexpected events, can therefore result in an increased risk with regard to seamless operation after restoration of the normal state, for example as a result of increased formation of deposits in apparatuses. There is therefore a need for a process for preparing isocyanates in which this risk is minimized by suitable precautions.

Taking account of this need, the present invention provides a continuous process for preparing an isocyanate (1) by reacting the corresponding amine (2) with phosgene (3) in an inert solvent (4) in a reaction section (1000) comprising
(a) a mixing zone (1100) for mixing amine (2), phosgene (3) and inert solvent (4)
and
(b) a reaction zone (1200) arranged downstream of the mixing zone (1100);
at a target temperature $T_{target}$, wherein the steps of
(A) starting up continuous production,
(B) continuous production and
(C) shutting down continuous production, and preferably
(D) displacing the phosgene (3) from the reaction section (1000)
are run successively, and wherein, in step (A),
  (I) the mixing zone (1100) and the reaction zone (1200) are at first at least partly charged
    (i) with inert solvent (4) only, then heated up to $T_{target}$ and then additionally charged with phosgene (3) but not with amine (2), preferably together with further inert solvent (4);
    or
    (ii) with inert solvent (4) and phosgene (3) without the amine (2) and then heated up to $T_{target}$;
  (II) only after step (A) (I) is the reaction zone (1200) supplied continuously with the amine (2) and also further phosgene (3) and further inert solvent (4) via the mixing zone (1100);
and, in step (C), the continuous production is shut down by first ending the supply of the amine (2) only, while continuous supply of phosgene (3) and inert solvent (4) still continues.

The reaction section (1000) refers to the part of a phosgenation plant in which the actual reaction of amine with phosgene to give the isocyanate takes place, i.e. the reaction part as opposed to the workup part (2000). One possible configuration of a reaction section 1000 (with connected workup section 2000) in the context of the present invention is shown by FIG. 1. Optional apparatuses are drawn with dotted lines. According to the invention, the reaction part comprises at least one mixing zone (1100) and at least one reaction zone (1200) arranged downstream of the mixing zone (1100). Arranged downstream of the mixing zone means that the output (5) of the mixing zone flows into the reaction zone (1200), with optional intermediate connection of a delay device (1110). In the process of the invention, during the performance of step (A) (I), no isocyanate is present in the reaction section (1000). Only with commencement of the amine supply in step (A) (II) does isocyanate (1) form for the first time. After step (C) has ended, the reaction section (1000) is free of isocyanate (1) again, and so the reaction section (1000) does not contain any isocyanate (1) from the prior production cycle during step (A) (I). Since no isocyanate (1) is initially charged in the reaction section (1000) either, there is accordingly no isocyanate (1) in the reaction section (1000) in the process of the invention during the performance of step (A) (I).

BRIEF DESCRIPTION OF THE DRAWING

FIG. 1 is an illustration of a configuration suitable for carrying out the processes of the invention.

DETAILED DESCRIPTION

Various embodiments of the invention are described in detail hereinafter. These may be combined with one another as desired, unless the context unambiguously suggests anything different to the person skilled in the art.

Step (A) of the process of the invention relates the startup operation of the reaction section (1000) proceeding from a non-operational phosgenation plant. In step (A) of the process of the invention, the starting state that exists in each case is converted to the state of production under normal conditions in such a way that the problems mentioned at the outset occur to a slight extent at most, if at all, as set out in detail hereinafter:

In a first embodiment of the process of the invention, the reaction section (1000) comprises just one mixing zone (1100) and a reaction zone (1200) arranged downstream thereof, both of which may also be combined in a single apparatus, and peripheral equipment such as pipelines, pumps, heaters and the like. Suitable apparatuses for the mixing zone (1100) are static or dynamic mixing apparatus as known to those skilled in the art, as detailed, for example, in EP 2 077 150 B1 (rotor-stator mixer; see particularly the drawings and the accompanying text passages) and in DE 37 44 001 C1 (mixing nozzle; see particularly the drawings and the accompanying text passages). Suitable apparatuses for the reaction zone (1200) are known to those skilled in the art, for example vertical tubular reactors preferably divided by horizontal perforated plates and optionally heatable—in the case of an isothermal process regime, optionally connected to a downstream separator for separation of gas phase and liquid phase, as described in EP 0 716 079 B1 with internals in the reactor or in EP 1 601 456 B1 without internals in the reactor.

Mixing zone and reaction zone are at least partly charged in step (A) (I) with inert solvent (4) and phosgene (3). Phosgene (3) is preferably supplied in the form of phosgene solution (30), i.e. a solution of phosgene (3) in the inert solvent (4), as shown in FIG. 1. The proportion by mass of phosgene (3) in this phosgene solution (30) is preferably 3.0% to 95%, more preferably 20% to 75%. For preparation of the phosgene solution (30), it is possible to employ suitable mixing apparatuses to mix phosgene (3) and inert solvent (4) (not shown in FIG. 1). Suitable apparatuses for the purpose are known from the prior art. Suitable inert solvents (4) according to the invention are solvents that are inert under the reaction conditions, for example monochlorobenzene, dichlorobenzene (especially the ortho isomer), dioxane, toluene, xylene, methylene chloride, perchloroethylene, trichlorofluoromethane or butyl acetate. The inert solvent (4) is preferably essentially free of isocyanate (target proportion by mass <100 ppm) and essentially free of phosgene (target proportion by mass <100 ppm), and this should be noted when using recycling streams. Preference is therefore given to working by a process as described in EP 1 854 783 A2. The solvents can be used individually or in the form of any desired mixtures of the solvents mentioned by way of example. Preference is given to using chlorobenzene or ortho-dichlorobenzene.

In variant (i), the mixing zone (1100) and the reaction zone (1200) are at first at least partly charged with inert solvent (4) and then heated up to the desired target temperature which preferably has a value of 80° C. to 130° C., more preferably of 95° C. to 115° C. The addition of the inert solvent (4) in this component step, as shown in FIG. 1, can be effected through the conduit that leads to the mixing of phosgene (3) and inert solvent (4), in which case the phosgene supply (3) is stopped during this operation. It is also possible (shown by dotted lines in FIG. 1) to provide a dedicated supply line for the inert solvent (4) only. Subsequently, the inert solvent (4) is admixed with phosgene (3), preferably as shown in FIG. 1 in the form of a phosgene solution (30), preferably for a sufficiently long period for a proportion by mass of phosgene (3) of 0.5% to 20%, more preferably of 1% to 10%, based on the total mass of phosgene (3) and inert solvent (4), to become established in the reaction zone (1200). As soon as the desired target temperature and the desired proportion by mass of phosgene (3) in the inert solvent (4) have been attained, the phosgenation is started by addition of amine (2), preferably as shown in FIG. 1 in the form of an amine solution (20), i.e. of a solution of the amine (2) in the inert solvent (4), and of further phosgene (3), preferably of further phosgene solution (30). The proportion by mass of the amine (2) in the amine solution (20) is preferably 5.0% to 95%, more preferably 20% to 70%. It has been found to be useful to purge the reaction section (1000) with inert solvent (4) prior to performance of step (A).

In variant (ii), inert solvent (4) and phosgene (3) are introduced into the mixing zone (1100) and the reaction zone (1200) before being heated up to the desired target temperature which, in this embodiment too, preferably has a value of 80° C. to 130° C., more preferably of 95° C. to 115° C. This is preferably accomplished in such a way that a solution of phosgene (3) in the inert solvent (4) is first prepared (phosgene solution (30)), where the proportion by mass of phosgene (3) in the inert solvent (4) is preferably 0.5% to 20%, more preferably from 1% to 10%, based on the total mass of phosgene and inert solvent. This phosgene solution (30) is introduced via the mixing zone (1100) into the reaction zone (1200), as shown in FIG. 1.

In both variants (i) and (ii), the procedure is preferably such that, at the end of step A (I), at least 50% by volume, preferably at least 80% by volume, more preferably at least 99% by volume and most preferably 100% by volume of the internal volume of the reaction zone (1200) available for the reaction of the amine (2) with phosgene (3) in the inert solvent (4) is charged with the mixture of amine (2), phosgene (3) and inert solvent (4). The "internal volume of the reaction zone (1200) available for the reaction of the amine (2) with phosgene (3) in the inert solvent (4)" in the reaction zone (1200) in the configuration according to FIG. 1 extends as far as the dotted line level with the conduit for the liquid crude product (61).

The addition of amine in step A (II) is not started until the mixing zone and reaction zone have been charged at least partly with inert solvent and phosgene and the target temperature of the reaction has been attained. The effect of this is that, at the start of step A (II), a very high molar excess of phosgene (3) over the amine (2) is present, which reduces the risk of formation of films and deposits on the apparatus walls in the reaction section.

Amines (2) which are suitable in accordance with the invention and can be converted by the process described to the corresponding isocyanates are methylenediphenyldiamine, polymethylenepolyphenylpolyamine, mixtures of methylenediphenyldiamine and polymethylenepolyphenylpolyamine, tolylenediamine, xylylenediamine, hexamethylenediamine, isophoronediamine and naphthyldiamine. Preference is given to methylenediphenyldiamine, mixtures of methylenediphenyldiamine and polymethylenepolyphenylpolyamine, and tolylenediamine.

In step (A) (II), it is preferable to prepare a solution of the amine (2) in an inert solvent (4) (amine solution (20)) and to feed it together with a solution of phosgene (3) in an inert solvent (4) (phosgene solution (30)) to the mixing zone (1100), as shown in FIG. 1. Appropriately, the same solvent (4) will be chosen for the amine and the phosgene, although this is not absolutely necessary. The proportion by mass of the amine (2) in the amine solution (20) is preferably 5.0% to 95%, more preferably 20% to 70%, based on the total mass of amine (2) and inert solvent (4). The proportion by mass of the phosgene (3) in the phosgene solution (30) is preferably 3.0% to 95%, more preferably 20% to 75%, based on the total mass of phosgene (3) and inert solvent (4).

The temperatures of the phosgene and amine solutions used are preferably adjusted prior to introduction into mixing zone (1200), specifically in such a way that the mixing temperature prior to onset of the phosgenation reaction or of the reaction of amine (2) and HCl formed to give the corresponding amine hydrochloride is sufficiently high to avoid separation of the amine solution into two phases. Such a phase separation leads to a local excess of amine, which can lead to increased formation of ureas from amine and phosgene and hence to increased formation of solids extending as far as blockage of the mixing apparatus. This phenomenon can be observed within particular temperature ranges. Preferably, therefore, the phosgene solution (30) has a temperature of −20° C. to +80° C., more preferably of −10° C. to +20° C. Most preferably, the temperature of the phosgene solution (30) is in the range from −5° C. to +10° C. The temperature of the amine solution (20) is preferably adjusted to +25° C. to +160° C., more preferably +40° C. to +140° C. Most preferably, the temperature of the amine solution is in the range from +50° C. to +120° C. Preferably, the temperature control and metered addition of the reactant solutions are effected at a pressure level above the vapor pressure of the particular solution. In this case, an absolute pressure of 1.0 bar to 70 bar, preferably of 2.0 bar to 45 bar and most preferably of 3 bar to 25 bar may be established.

Concentrations and flow rates of the amine and phosgene reactants in step (A) (II) are preferably chosen such that, in the mixing zone (1100), after complete displacement of the mixture of amine (2), phosgene (3) and inert solvent (4) initially charged in step A (I), a molar ratio of phosgene to primary amino groups of 1.1:1 to 30:1, more preferably of 1.25:1 to 3:1, is established.

In a second embodiment of the process of the invention, an additional delay device (1110; shown by dotted lines in FIG. 1) for optimization of the mixing of the amine and phosgene reactants is present between the mixing zone (1100) and reaction zone (1200). In the simplest case, this is a pipe, the diameter and length of which are matched to the desired production capacity of the reaction section (1000). The inert solvent (4) and phosgene (3) reactants to be added in step (A) (I) pass via the mixing zone (1100) through the delay device (1110) into the reaction zone (1200), meaning that the delay device 1110, prior to the addition of amine, is also charged, preferably fully, with inert solvent and phosgene as per variant (i) or (ii), in order to be able to charge the reaction zone (1200) at least partly with inert solvent and phosgene. All the preferred ranges specified for the first embodiment (solvent purity, pressure, temperature, proportion by mass of amine and phosgene in the respective solutions, molar ratio of phosgene to primary amino groups) apply equally to this embodiment. The same applies to the feedstocks and apparatuses designated as preferred.

In a third embodiment of the process of the invention, which can be combined with the two aforementioned embodiments, connected downstream of the reaction zone (1200) is an apparatus (1300) for cleavage of the carbamoyl chloride intermediate that occurs in liquid phase phosgenations of amines (shown by dotted lines in FIG. 1). This is advantageous when the liquid crude product (61) which is obtained after removal of the hydrogen chloride- and phosgene-containing gas phase (71) and exits from the reaction zone (1200) still contains substantial proportions of uncleaved carbamoyl chloride. Suitable apparatuses 1300 are known to those skilled in the art; examples in which the liquid film is produced mechanically include, for example, what are called SAMBAY and LUWA thin-film evaporators, and also Sako thin-film evaporators and ALFA-LAVAL Centritherm evaporators. It is also possible to use layer evaporators having no moving parts. Examples of these are falling-film evaporators (also referred to as falling-stream evaporators or falling-layer evaporators) or else helical tube evaporators and climbing-film evaporators. In the apparatus 1300, carbamoyl chloride still present in the liquid crude product 61 is cleaved to give the desired isocyanate and hydrogen chloride. In the apparatus 1300, an isocyanate-containing liquid stream (62) and a gas stream (72) comprising hydrogen chloride (with or without excess phosgene) are thus obtained.

In this embodiment, charging of the apparatus 1300 with phosgene (3) and inert solvent (4) before the addition of the amine (2) is started in step (A) (II) is not absolutely necessary. All the preferred ranges specified for the first embodiment (solvent purity, pressure, temperature, proportion by mass of amine and phosgene in the respective solutions, molar ratio of phosgene to primary amino groups) apply equally to this embodiment. The same applies to the feedstocks and apparatuses designated as preferred.

On attainment of the desired operating state, the continuous production of isocyanate (step (B)) is effected in the reaction section (1000). Step (B) can be conducted by a process known from the prior art. Suitable processes are described, for example, in EP 1 616 857 A1, EP 1 873 142 A1, EP 0 716 079 B1 or EP 0 314 985 B1, and these can in principle be applied without any particular precautions to step (B) of the process of the invention. However, concentrations and flow rates of the amine (2) and phosgene (3) reactants are preferably chosen such that a molar ratio of phosgene to primary amino groups of 1.1:1 to 30:1, more preferably of 1.25:1 to 3:1, is established in the mixing zone (1100). In addition, the preferred configurations described for step (A) relating to solvent purity, pressure, temperature, proportion by mass of amine and phosgene in the respective solutions, are preferably also observed in step (B).

All processes for the continuous production of an isocyanate in the liquid phase afford a crude product comprising a liquid phase containing, as well as the desired isocyanate, dissolved hydrogen chloride and excess dissolved phosgene, and also a gas phase containing hydrogen chloride gas and excess phosgene. After the gas phase 71 has been removed (for example on exit from the reaction zone (1200) as shown in FIG. 1 or in a suitable separator which follows the reaction zone), what remains is a liquid crude isocyanate solution (61) which, optionally after passing through an apparatus for cleavage of carbamoyl chloride (1300), is worked up further by methods known from the prior art (removal of the solvent, fine purification of isocyanate shown in FIG. 1 purely in schematic form as a workup zone 2000), in order to obtain the desired isocyanate (1) in maximum purity. Suitable processes are described in EP 1 854 783 A2 and EP 1 506 957 A1, or else in EP 1 371 635 B1.

The person skilled in the art is aware that a production which is continuous in principle cannot be operated for an arbitrarily long period, but has to be stopped at particular intervals, for example to conduct maintenance operations. The shutdown of a continuous isocyanate production in a manner which avoids or at least minimizes the problems cited at the outset on restart is the subject of step (C) of the process of the invention.

What is essential to the invention is that the continuous production is shut down by first ending the supply of the amine (2) only, while continuous supply of phosgene (3) and inert solvent (4) still continues for a period of time $t_c$. By virtue of continuing application of phosgene (3) and inert solvent (4), preferably in the form of a phosgene solution (30), a huge excess of phosgene is achieved, by virtue of which all the intermediates still present in the reaction section (1000), such as amine hydrochloride and carbamoyl chloride, are depleted by reaction. Preferably, the period of time $t_c$ is chosen such that the internal volume of the reaction zone (1200) available for the reaction of the amine (2) with phosgene (3) in the inert solvent (4) is run through 0.1 time to 10 times, preferably 1 time to 5 times, by phosgene (1) and inert solvent (4), preferably in the form of the phosgene solution (30). In the event of compliance with these values, the mixture generally runs significantly more frequently through the mixing zone (1100) and, if present, the delay apparatus (1110), since these are generally much smaller than the reaction zone (1200). The more thoroughly this operation is conducted, the lower the risk of formation of films and deposits. In the course of this, the reaction section (1000) may be heated wholly or partly by means of industrial heating, the maximum temperatures maintained preferably being those from the continuous mode of operation (step (B)). After performance of step (C), only phosgene (3) and inert solvent (4) are thus still present in the reaction section. Isocyanate (1) and any unconverted amine (2) present and any intermediates present are purged out of the reaction section by step (C).

After the desired exchange of volume in step (C), it is preferable to finally displace, in a step (D), the phosgene (3) from the reaction section (1000) with inert solvent (4). For this purpose, at first the supply of phosgene (3) only is ended, while continuous supply of inert solvent still continues. To achieve a lasting effect, the duration $t_D$ of this solvent wash should preferably be chosen such that the internal volume of the reaction zone (1200) available for the reaction of the amine (2) with phosgene (3) in the inert solvent (4) is run through 0.1 time to 10 times, more preferably 1 time to 5 times, by inert solvent (4). In the event of compliance with these values, the solvent generally runs significantly more frequently through the mixing zone (1100) and, if present, the delay apparatus (1110), since these are generally much smaller than the reaction zone (1200). Purge durations of several days may also be employed and may be advantageous in the context of the present invention. The amount of solvent and purge duration to be chosen depends not only on the apparatus volume of the reaction section (1000) including peripheral equipment but also, if they are not completely avoidable, on the amount of any deposits present.

The procedure of the invention gives rise to the following advantages for the preparation of isocyanates:

i) The productivity of the reaction section is higher because fewer cleaning periods are needed.

ii) The productivity of the reaction section is higher because fewer pressure drops occur in the mixing apparatuses and pipelines.

iii) The energy efficiency of the reaction section is higher because fewer deposits on the apparatus walls assure better heat transfer.

iv) A lower level of waste arises after the cleaning of the reaction section (minimized polyurea formation).

v) The formation of solids which can impair the downstream apparatuses such as pumps and columns by abrasion or deposits is minimized.

Thus, the process of the invention enables, by ensuring a huge excess of phosgene (3) over the amine (2) on commencement of step A (II), a technically seamless start of the reaction section without downtime with a directly high end product quality of the desired isocyanate. The process of the invention also enables a more rapid startup and hence a quicker rise in the amine flow rate and hence increased production.

EXAMPLES

General Conditions for the Preparation of a Mixture of Methylene Diphenyl Diisocyanate and Polymethylene Polyphenyl Polyisocyanate (Collectively MDI Hereinafter) with a "Run-In" Production Plant (Corresponding to Step (B) of the Process of the Invention)

4.3 t/h of a mixture of methylenediphenyldiamine and polymethylenepolyphenylpolyamine (collectively MDA hereinafter; 2) at a temperature of 110° C. are mixed with 11 t/h of monochlorobenzene (MCB; 4) at a temperature of 30° C. as solvent by means of a static mixer (1100) to give a 28% MDA solution (20). Phosgene (3) is provided by means of a phosgene generator and a phosgene liquefier. Thereafter, the phosgene (3) is diluted to a 35% phosgene solution (30) with MCB (4) in a phosgene dissolution tank. 24 tonnes per hour of 35% phosgene solution (30) at a temperature of 0° C. are reacted with 4.3 tonnes per hour of MDA (2) in the form of the 28% MDA solution (20) at a temperature of 45° C. in an adiabatic reaction, as described in EP 1 873 142 B1. After the two raw material solutions have been mixed in the mixing apparatus (1100), the reaction solution (5) obtained is run at a temperature of 85° C. through a suspension conduit (1200) into a heated phosgenation tower (1200). At the top of the phosgenation tower, the absolute pressure is 1.6 bar and the temperature is 111° C. The hydrogen chloride formed in the reaction is removed together with traces of phosgene and MCB as gas stream (71). The liquid reaction mixture (61) is withdrawn from the phosgenation tower (1200) and fed to the workup sequence (2000). For this purpose, it is first introduced as a sidestream into a heated dephosgenation column. At a top temperature of 116° C. and an absolute pressure of 1.6 bar, phosgene is removed overhead together with traces of MCB and hydrogen chloride. Phosgene is absorbed in a phosgene absorption column and run into the phosgene dissolution tank, and hydrogen chloride is directed into a hydrogen chloride absorber and then into a hydrochloric acid tank for further use. After removal of hydrogen chloride and excess phosgene from the isocyanate-containing reaction solution, a crude isocyanate solution is obtained, which is discharged from the bottom of the dephosgenation column and run at a temperature of 155° C. into a first distillation stage, in order to free it of the MCB solvent. The absolute pressure at the top of this solvent distillation column is 800 mbar at a bottom temperature of 155° C. MCB is drawn off in gaseous form overhead, this MCB gas stream being sprayed with cold MCB (30° C.) in a scrubbing column, in order to prevent any possible entrainment of isocyanate into the vacuum conduits. The reaction product is discharged from the bottom of the column and freed of residual MCB down to 1% in a second column. Subsequently, in a countercurrent evaporator, at an absolute pressure of 20 mbar and a bottom temperature of 210° C., the product is freed of secondary components such as phenyl isocyanate and residual MCB. This affords 5.4 t/h of MDI as bottom product, which is worked up by means of further distillation to give MDI of the desired purity (1) and then run into a tank for further use.

MDI prepared in this way has a residual MCB solvent content of <5 ppm (GC), a content of hydrolyzable chlorine of <100 ppm (after solvolysis by means of titration) and a content of bound chlorine of <50 ppm (Wickbold combustion).

Example 1 Comparative Example, Step (C) Noninventive

The preparation of 5.4 t/h of MDI in continuous mode was conducted at nameplate load as described in the general conditions. The plant was shut down, with simultaneous abrupt stoppage of the phosgene solution and MDA solution supply. The reactor was allowed to cool down, while keeping the reactor pressure constant with nitrogen. After one day of repair operations on another part of the plant, the phosgenation plant was started up by filling the plant with solvent up to the level of the withdrawal conduit for the crude product (61) and heated up to 105° C. with the aid of a heat transfer agent. The phosgene solution supply was put into operation with a load of 25% of the nameplate load. After one hour, the MDA solution supply was started with a load of 15% of the nameplate load, which corresponded to a production output of 0.8 t/h (MDI). The two streams were then to be increased to nameplate load within two hours. This was not possible because of baked-on solids which had formed in the region of the phosgenation reactor and in the mixing apparatus after the abrupt shutdown. The supply pressure available for the reactants 20 and 30 was no longer sufficient to attain the desired nameplate load. The plant had to be shut down and the regions covered with solids cleaned.

Example 2 Comparative Example, step (A) Noninventive

The preparation of 5.4 t/h of MDI in continuous mode was conducted at nameplate load as described in the general conditions. The plant was shut down by first stopping the MDA supply. MCB from the MDA solution supply and the phosgene solution continued to run with the previous nameplate load volume for one hour. Subsequently, the phosgene supply was stopped, and the plant was freed of phosgene with a two-hour purge with MCB. The temperature of the phosgenation plant was kept at 110° C. by means of industrial heating. Then the phosgenation plant was allowed to cool down, while keeping the plant pressure constant with nitrogen. After several days of repair operations on another part of the plant, the phosgenation plant was started up by filling the plant with solvent up to the level of the withdrawal conduit for the crude product (61) and heated up to 105° C. with the aid of a heat transfer agent. The phosgene solution and MDA solution supply were switched on simultaneously. The plant was started at 15% of the nameplate capacity, which corresponded to a production output of 0.8 t/h (MDI). The flow rates were then increased to nameplate load within two hours, and the plant was transferred to continuous mode (step (B)). After a further five hours at nameplate load, the phosgenation plant had to be shut down completely because the distributor trays of the dephosgenation column began to become blocked, and the pressure drop over the column rose as a result. The plant had to be shut down in order to free the dephosgenation column of baked-on urea and loose urea present in the column, and to prepare it for a restart.

Example 3 (Inventive)

The preparation of 5.4 t/h of MDI in continuous mode was conducted at nameplate load as described in the general conditions. The plant was shut down by first stopping the MDA supply. MCB from the MDA solution supply and the phosgene solution continued to run with the previous nameplate load volume for one hour. Subsequently, the phosgene supply was stopped, and the plant was freed of phosgene with a two-hour purge with solvent. The temperature of the phosgenation plant was kept at 110° C. by means of industrial heating. Then the phosgenation plant was allowed to cool down, while keeping the plant pressure constant with nitrogen. After several days of repair operations on another part of the plant, the phosgenation plant was started up by filling the plant with solvent up to the level of the withdrawal conduit for the crude product (61) and heated up to 105° C. with the aid of a heat transfer agent. The phosgene solution supply was put into operation with a load of 25% of the nameplate load. After one hour, the MDA solution supply was started with a load of 15% of the nameplate load, which corresponded to a production output of 0.8 t/h (MDI). The two flow rates were then increased to nameplate load within two hours, and then the phosgenation plant was operated for several months as described in the general conditions. Startup was possible directly with on-spec material.

As the examples show, when baked-on material is already present in the phosgenation reactor during the startup of the phosgenation, great problems arise with the reactant supply into the plant. In the case of the inventive procedure in the startup and shutdown of the phosgenation, by contrast, the formation of baked-on material and precipitates is distinctly reduced, the plant can be operated over a long production cycle, and on-spec material is produced over the whole period.

The invention claimed is:

1. A continuous process for preparing an isocyanate by reacting the corresponding amine with phosgene in an inert solvent in a reaction section comprising:
    (a) a mixing zone for mixing amine, phosgene and inert solvent
    and
    (b) a reaction zone arranged downstream of the mixing zone;
at a target temperature, wherein the process comprises
(A) starting up continuous production,
(B) continuous production and
(C) shutting down continuous production
wherein (A), (B) and (C) are run successively, and wherein, in step (A),
    (I) the mixing zone and the reaction zone are at first at least partly charged
        (i) with inert solvent only, then heated up to the target temperature and then additionally charged with phosgene but not with amine;
    or
        (ii) with inert solvent and phosgene without the amine and then heated up to the target temperature;
    (II) only after step (A)(I) is the reaction zone supplied continuously with the amine and also further phosgene and further inert solvent via the mixing zone;
and, in step (C), the continuous production is shut down by first ending the supply of the amine only, while continuous supply of phosgene and inert solvent still continues.

2. The process of claim 1, in which an additional delay device is present between the mixing zone and reaction zone.

3. The process of claim 1, in which the reaction zone has a downstream apparatus for cleaving carbamoyl chloride.

4. The process of claim 1, in which, after step (C), step (D) comprising displacing the phosgene from the reaction section is run, which is conducted by at first ending the supply of phosgene only, while continuous supply of inert solvent still continues.

5. The process of claim 1, in which the target temperature has a value of 80° C. to 130° C.

6. The process of claim 1, in which, in step (A)(I), a proportion by mass of phosgene of 0.5% to 20%, based on the total mass of phosgene and inert solvent, is established.

7. The process of claim 1, wherein, at the end of step (A)(I), at least 50% by volume of the internal volume of the reaction zone available for the reaction of the amine with phosgene in the inert solvent is charged with the mixture of amine, phosgene and inert solvent.

8. The process of claim 1, in which, in step (C), the supply of phosgene and inert solvent is still continued for a period of time that is chosen such that the internal volume of the reaction zone available for the reaction of the amine with phosgene in the inert solvent is run through 0.1 time to 10 times.

9. The process of claim 4, in which, in step (D), after the supply of phosgene has ended, inert solvent is still supplied continuously for a period of time that is chosen such that the internal volume of the reaction zone available for the reaction of the amine with phosgene in the inert solvent is run through 0.1 time to 10 times.

10. The process of claim 1, wherein, in the mixing zone, after complete displacement of the mixture of amine, phosgene and inert solvent initially charged in step A (I), a molar ratio of phosgene to primary amino groups of 1.1:1 to 30:1 is established.

11. The process of claim 1, in which the amine is selected from the group consisting of methylenediphenyldiamine, polymethylenepolyphenylpolyamine, a mixture of methylenediphenyldiamine and polymethylenepolyphenylpolyamine, tolylenediamine, xylylenediamine, hexamethylenediamine, isophoronediamine and naphthyldiamine.

12. The process of claim 11, in which the amine is methylenediphenyldiamine or a mixture of methylenediphenyldiamnine and polymethylenepolyphenylpolyamine or tolylenediamine.

13. The process of claim 11, in which the amine is methylenediphenyldiamine or a mixture of methylenediphenyldiamine and polymethylenepolyphenylpolyamine.

14. The process of claim 11, in which the amine is tolylenediamine.

15. The process of claim 1, in which the inert solvent is selected from the group consisting of monochlorobenzene, dichlorobenzene, dioxane, toluene, xylene, methylene chloride, perchloroethylene, trichlorofluoromethane and butyl acetate.

16. The process of claim 5, in which the target temperature is from 95° C. to 115° C.

17. The process of claim 6, in which, in step (A)(I), a proportion by mass of phosgene of 1% to 10%, based on the total mass of phosgene and inert solvent, is established.

18. The process of claim 7, wherein, at the end of step (A)(I), at least 80% by volume of the internal volume of the reaction zone available for the reaction of the amine with phosgene in the inert solvent is charged with the mixture of amine, phosgene and inert solvent.

19. The process of claim 7, wherein, at the end of step (A)(I), at least 99% by volume of the internal volume of the reaction zone available for the reaction of the amine with phosgene in the inert solvent is charged with the mixture of amine, phosgene and inert solvent.

20. The process of claim 7, wherein, at the end of step (A)(I), 100% by volume of the internal volume of the reaction zone available for the reaction of the amine with phosgene in the inert solvent is charged with the mixture of amine, phosgene and inert solvent.

21. The process of claim 8, wherein the internal volume of the reaction zone available for the reaction of the amine with phosgene in the inert solvent is nm through 1 time to 5 times by phosgene and inert solvent.

22. The process of claim 8, wherein the phosgene and inert solvent is in the form of a solution of phosgene in the inert solvent.

23. The process of claim 9, wherein the internal volume of the reaction zone available for the reaction of the amine with phosgene in the inert solvent is run through 1 time to 5 times by inert solvent.

24. The process of claim 10, wherein, in the mixing zone, after complete displacement of the mixture of amine, phosgene and inert solvent initially charged in step A (I), a molar ratio of phosgene to primary amino groups of 1.25:1 to 3:1, is established.

\* \* \* \* \*